(12) United States Patent
Neubardt

(10) Patent No.: US 8,147,246 B2
(45) Date of Patent: Apr. 3, 2012

(54) SURGICAL BONE WAX APPLICATOR

(76) Inventor: Seth L. Neubardt, Mamaroneck, NY (US)

( * ) Notice: Subject to any disclaimer, the term of this patent is extended or adjusted under 35 U.S.C. 154(b) by 1815 days.

(21) Appl. No.: 11/091,089

(22) Filed: Mar. 28, 2005

(65) Prior Publication Data

US 2006/0216671 A1    Sep. 28, 2006

(51) Int. Cl.
*A61C 13/225*    (2006.01)

(52) U.S. Cl. .................................................. 433/172

(58) Field of Classification Search .................. None
See application file for complete search history.

(56) References Cited

U.S. PATENT DOCUMENTS

| | | | |
|---|---|---|---|
| 683,098 A | | 9/1901 | Baecker |
| 3,596,657 A | * | 8/1971 | Eidus ................................ 602/2 |
| 5,201,704 A | * | 4/1993 | Ray ................................ 604/500 |
| 5,250,046 A | * | 10/1993 | Lee ................................ 606/29 |
| 5,306,287 A | * | 4/1994 | Becker ................................ 606/205 |
| 5,374,246 A | * | 12/1994 | Ray ................................ 604/500 |
| 5,383,879 A | * | 1/1995 | Phillips ................................ 606/86 R |
| 5,482,717 A | | 1/1996 | Fues et al. |
| 5,685,879 A | | 11/1997 | Phillips |
| 6,203,541 B1 | * | 3/2001 | Keppel ................................ 606/38 |
| 6,231,574 B1 | | 5/2001 | Posthuma |
| 6,695,837 B2 | * | 2/2004 | Howell ................................ 606/29 |

* cited by examiner

*Primary Examiner* — Shanon A Foley
(74) *Attorney, Agent, or Firm* — Law Office of Leo Zucker

(57) ABSTRACT

A surgical bone wax applicator includes one or more layers of absorbent material such as cotton, and a mass of bone wax adhered on the material. A heating device such as, for example, a resistive electrical conductor is fixed on or within the absorbent material. The heating device has associated electrical contact terminals and operates to heat and soften the bone wax in response to an electric potential applied across the terminals. The potential may be applied through blades of bipolar forceps after the forceps are connected to a bipolar generator, and the forceps blades are placed in contact with the terminals of the heating device. When the wax softens, the surgeon may continue to grip the applicator with the forceps and manipulate the applicator over the pores of bone tissue to effect hemostasis.

20 Claims, 3 Drawing Sheets

US 8,147,246 B2

SURGICAL BONE WAX APPLICATOR

BACKGROUND OF THE INVENTION

1. Field of the Invention

This application relates generally to surgery, and particularly to an apparatus and technique for applying bone wax during a surgical procedure.

2. Discussion of the Known Art

U.S. Pat. No. 5,374,246 (Dec. 20, 1994) discloses a method and a device for delivering a hemostatic agent onto a patient's bone tissue during surgery. A mass of bone wax is attached on a surface of a strip of absorbent material, e.g., a "Cottonoid"®. Prior to use, the bone wax is heated so that it becomes soft enough to enter pores of the bone tissue when the Cottonoid is gripped with forceps and pressed against the bone tissue to effect hemostasis. A water bath is preset to a temperature sufficient to soften the wax on the Cottonoid, and each Cottonoid/bone wax combination must be immersed in the bath prior to use. See also U.S. Pat. No. 5,685,879 (Nov. 11, 1997), which discloses a surgical bone wax applicator in the form of a footplate with a handle, and with bone wax adhered on a bottom surface of the footplate.

An arrangement and technique wherein quantities of bone wax can be applied to bone tissue without a requirement for a heated water bath or other external heating means, would be highly desirable.

SUMMARY OF THE INVENTION

According to the invention, a surgical bone wax applicator includes one or more layers of absorbent material, and a mass of bone wax adhered on an outside surface of the material. A heating device is fixed on or within the absorbent material. The heating device is constructed and arranged to heat and soften the bone wax when the heating device is energized.

Other features, objects and advantages of the present invention will be apparent to those skilled in the art in view of the following specification when taken in conjunction with the accompanying drawing and the appended claims.

DETAILED DESCRIPTION OF THE INVENTION

Figure 1:
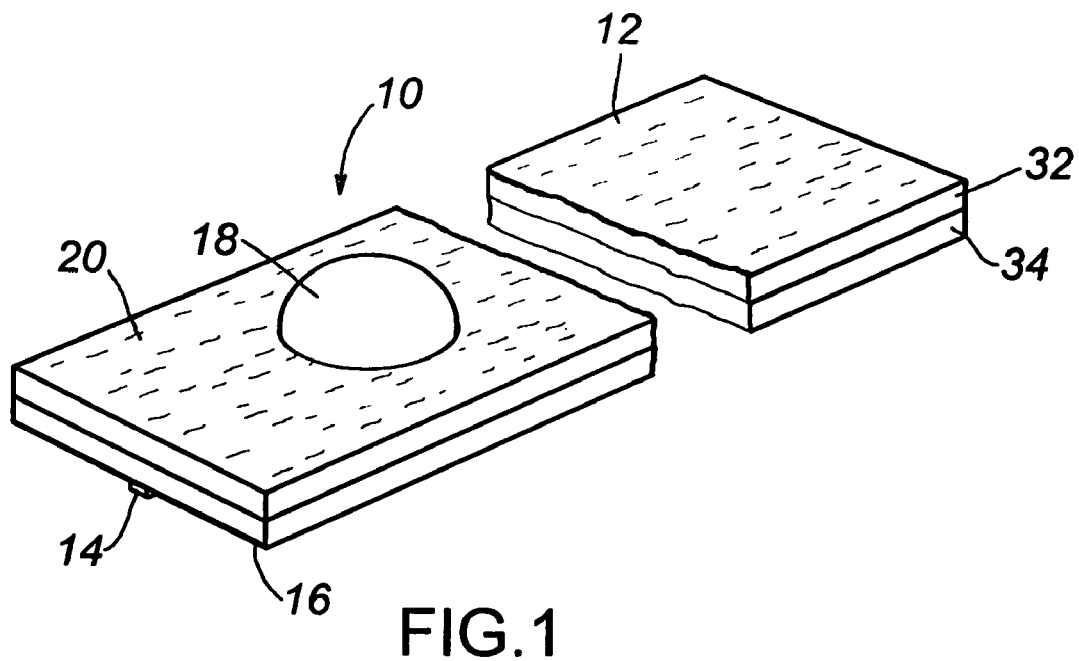
FIG. 1 is a perspective view of a surgical bone wax applicator according to the invention.

FIG. 1 shows a surgical bone wax applicator 10 according to the invention. The applicator 10 is constructed with one or more layers of a soft, surgically safe absorbent material 12 such as cotton. The material 12 is preferably treated to be flame resistant or retardant, for example, "Indura"® treated cotton. The overall size of the applicator 10 may be the same or similar to that of currently available Cottonoid strips, for example, one-half inch wide by up to six inches long. For spinal surgical use, it may be preferable that the length of the applicator 10 not exceed about five inches.

A radiopaque strip marker 14 is provided on a lower surface 16 of the applicator 10 such that the marker 14 is aligned medially between the long side edges of the applicator. The marker 14 will be highly visible in post-operative X-ray imaging if the applicator 10 is inadvertently allowed to remain inside a patient after surgery.

As seen in FIG. 1, a mass of bone wax 18 is adhered on an upper surface 20 of the applicator 10, toward one end of the applicator as shown in the drawing. The wax may be deposited initially in a softened state on the surface of the applicator such that the wax solidifies into globular form, and adheres to the fibers of the applicator material 12 on and below the upper surface 20 of the applicator 10.

Figure 2:
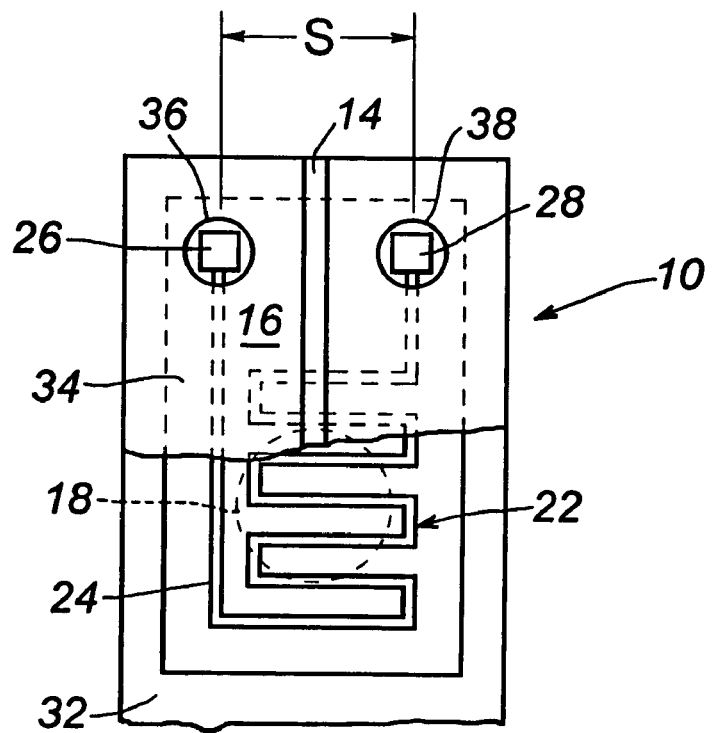
FIG. 2 is a bottom view of the applicator in FIG. 1.

A heating device 22 is disposed on or within the material 12 of the applicator 10, in the vicinity of the deposited bone wax 18. In the present embodiment, the heating device 22 is in the form of a resistive heating wire or conductor 24 that extends in a serpentine path beneath the bone wax 18 and is terminated at both ends with a pair of electrical contact terminals 26, 28 as shown in FIG. 2. The terminals 26, 28 are exposed on the lower surface 16 of the applicator 10, for example, at either side of the radiopaque marker 14 as seen at the top of FIG. 2. As explained later below, a spacing S between the terminals 26, 28 preferably does not exceed a typical rest spacing between confronting blades of conventional bipolar forceps.

Figure 3:
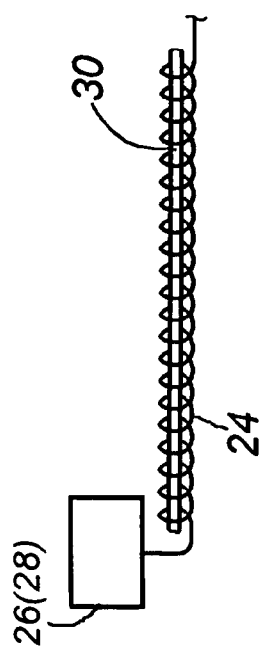
FIG. 3 is a partial view of a heating device in the applicator.

The heating conductor 24 should present an impedance or electrical load between the terminals 26, 28 such as to allow sufficient current to flow through the conductor 24 to heat the conductor just enough to soften the bone wax 18, so that the wax can be urged into pores of bone tissue by manipulating the applicator 10 with the mentioned bipolar forceps. Examples of such conductors include, without limitation, nickel-chrome alloys and iron-chrome alloys in wire or ribbon form and available from Hyndman Industrial Products Inc., Fort Wayne, Ind. (www.resistancewire.com). For example, as seen in FIG. 3, a resistive wire 24 of a gage between about 35 and 45 AWG may be tightly coiled about a heat resistant thread or cord 30. The overall length of the wire 24 between the terminals 26, 28 should provide enough electrical resistance to prevent excessive current flow when a potential is applied to the terminals by blades of conventional bipolar forceps.

In the illustrated embodiment, the applicator 10 comprises two absorbent material layers 32, 34. It is contemplated that a multi-layer construction will allow the serpentine heating conductor 24 to be disposed between confronting plies or layers of the absorbent material 12. Whether in ribbon, wire or coiled form, the conductor 24 may also be formed on a separate thin strip of electrically insulated heat resistant material as seen in FIG. 2. In the latter case, the terminals 26, 28 may be disposed on the separate strip, and be formed to project through corresponding holes 36, 38 that are cut, e.g., in the lower material layer 34 as shown in FIG. 2.

Figure 4:
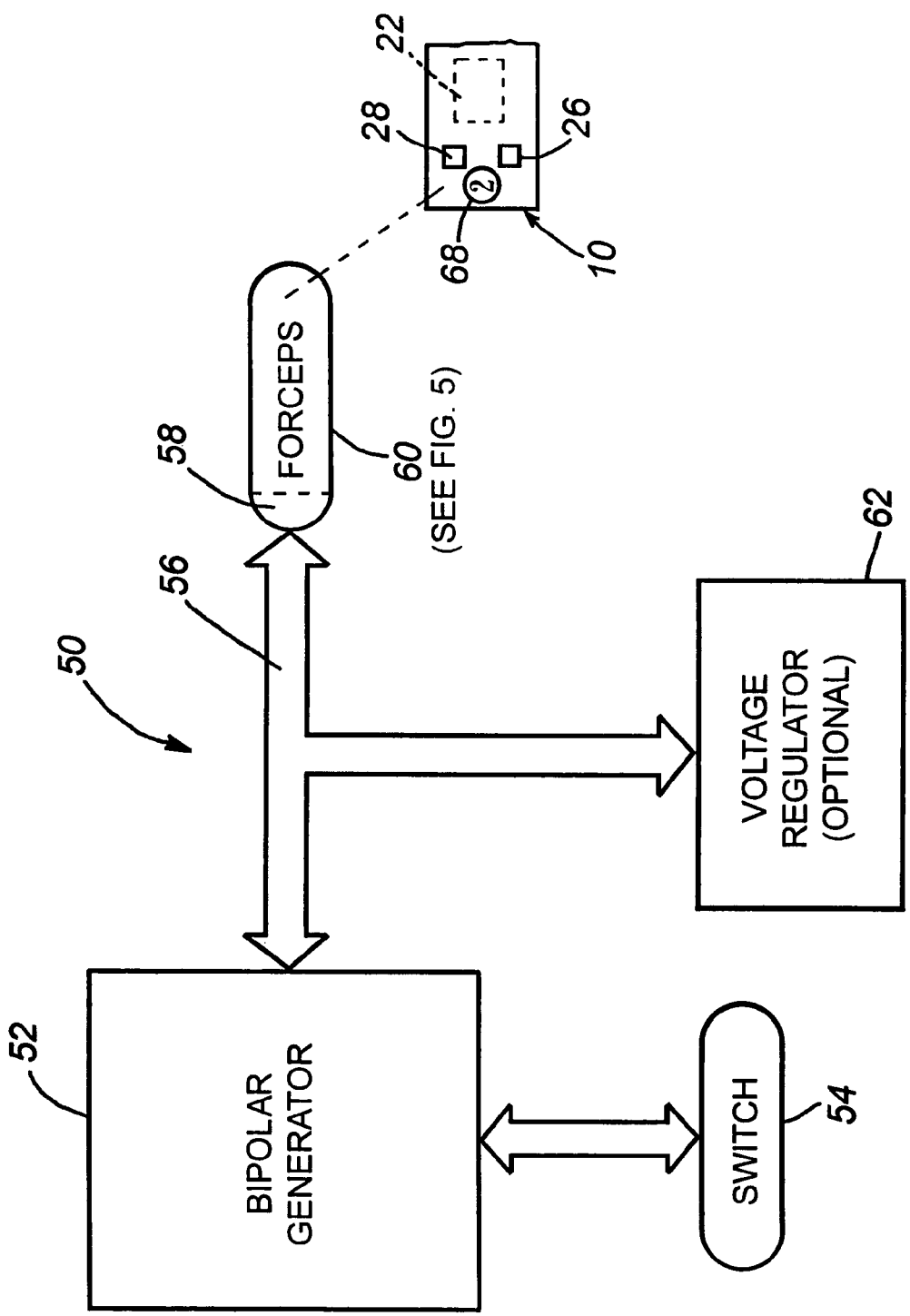
FIG. 4 is a schematic block diagram of an electrical operating system for the applicator.

FIG. 4 is a schematic block diagram of an electrical operating system 50 for the bone wax applicator 10 of FIGS. 1-3. The system 50 includes a bipolar generator 52. The generator 52 may be one of a number of commercially available bipolar generators such as, for example, ELMED Model BC 50 M/M; Wet-Field® No. 221320, or the like. Such generators typically have a low radio frequency (RF) power output that is adjustable from less than one watt to as much as 50 watts into a non-inductive load of approximately 100 to 500 ohms. The generator 52 may be operated manually by a surgeon using, e.g., a foot switch 54, a hand switch, or other means not shown in the drawing. The output of the generator 52 is applied through a cable 56 to a power input connector 58 of bipolar forceps 60. See FIG. 5. A voltage regulator 62 may be provided if necessary to ensure that power transmitted from the generator 52 to the forceps 60 will not exceed a level that might possibly overload the heating device 22 in the bone wax applicator 10. Regulator 62 may be provided externally, or be integrated with the circuitry of the generator 52. It will be understood that protective power regulation may also be provided within the heating device 22 of the bone wax applicator including, for example, one or more Zener diodes or varistors.

Figure 5:
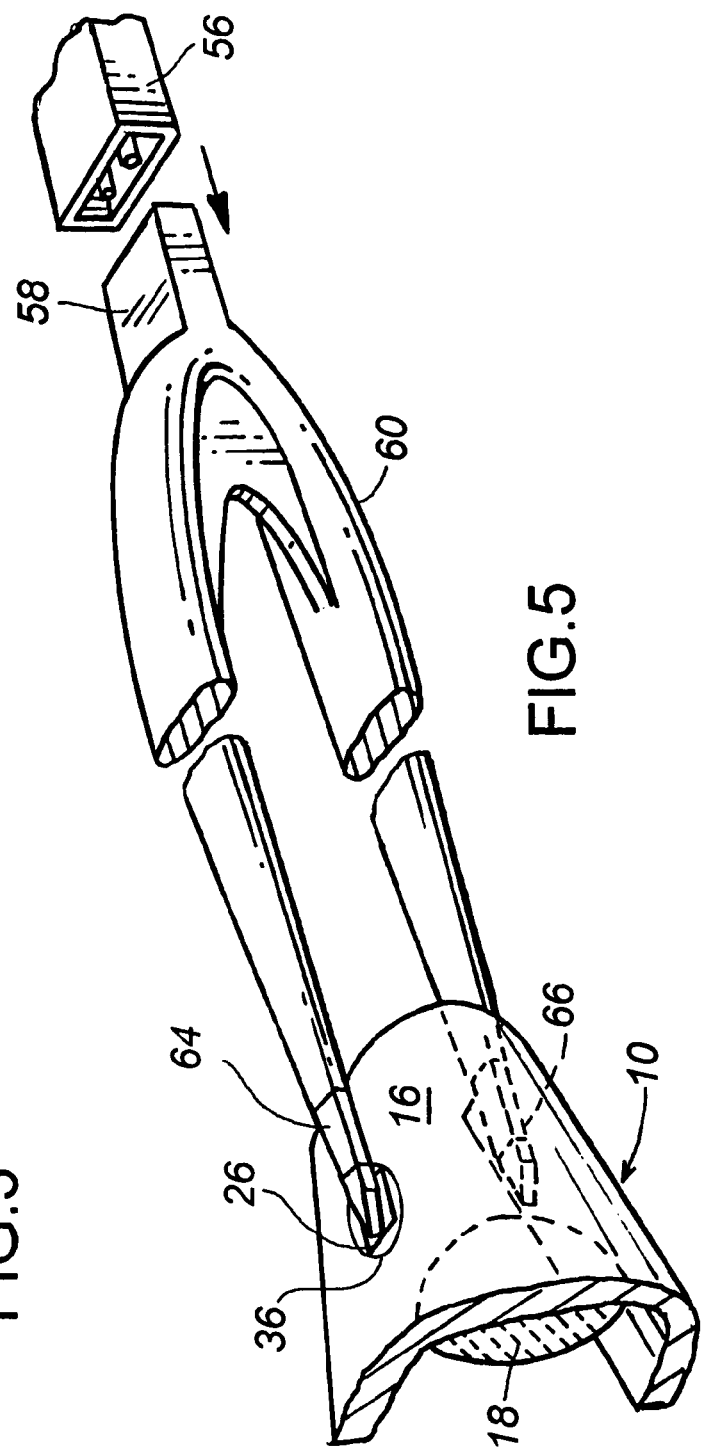
FIG. 5 shows the applicator when gripped with bipolar forceps according to the invention.

FIG. 5 shows opposing electrical contact blades 64, 66 of the forceps 60, in contact with corresponding contact terminals 26, 28 of the heating device inside a given bone wax applicator 10. In use, the surgeon holds the forceps 60 and grasps the applicator 10 by placing the opened, opposing blades 64, 66 of the forceps on the contact terminals 26, 28 of the applicator 10. The bipolar generator 52 is then activated so that the output voltage of the generator is applied across the terminals 26, 28 and a corresponding current is caused to flow in the heating device 22 of the applicator. The mass of bone wax 18 is then heated and softens enough so that while continuing to grasp the applicator with the forceps 60, the surgeon can apply the bone wax by manipulating the applicator over exposed porous bone tissue to effect hemostasis. When the bone wax on a given applicator is depleted, the surgeon merely releases the used applicator from the forceps and closes the forceps blades onto the contact terminals of a new applicator.

It will be appreciated that the inventive bone wax applicator 10 obviates the need for a heated water bath or other external means in order to heat bone wax to a proper temperature for application. By dispensing with the need to attend to such outside heating means, the attention of the operating personnel will not be distracted from the patient's operating situs, and any likelihood of surgical error is reduced.

To help the operating room personnel to account for all of the bone wax applicators 10 used during a given operation, the applicators may be packaged in boxes of, for example, ten applicators per box with each applicator having a different identifier 68 clearly printed or marked on an outside surface as shown in FIG. 4. For example, each applicator in a box of ten may be marked with a single numerical digit between 0 and 9. Further, the print style or font used for the identifiers may vary from box to box, thus making it easier for the personnel to account for all of the applicators if two or more boxes were opened during the operation.

While the foregoing represents a preferred embodiment of the invention, it will be understood by those skilled in the art that various modifications and changes may be made without departing from the spirit and scope of the invention, and that the invention includes all such modifications and changes as are within the scope of the following claims. For example, during surgery and after bloodying one end of an absorbent strip, it is not unusual for the surgeon to "flip" the strip around and use the opposite clean end of the strip before retrieving a new strip. Accordingly, separate masses of bone wax may be adhered at or near the opposite ends of the strip, with each wax mass having an associated heating device on or within the material. In addition, for instances where one wax mass is insufficient to cover a large bone surface area to be treated, two or more bone wax masses may be provided at or near each end of the absorbent strip, each with an associated heating device.

I claim:

1. A surgical bone wax applicator, comprising:
   one or more layers of absorbent material;
   a mass of bone wax deposited on a surface of the absorbent material so that the bone wax adheres to the material;
   an electrical heating element comprising an electrically resistive heating wire or conductor that extends within the absorbent material in the vicinity of the mass of bone wax, and the heating wire has an associated pair of electrical contact terminals that are exposed on the applicator for connecting the heating wire to an outside voltage source; and
   the heating wire is constructed and arranged to heat and soften the mass of bone wax when the electrical contact terminals of the heating wire are connected to the outside voltage source and a determined current flows through the heating wire.

2. A surgical bone wax applicator according to claim 1, wherein the exposed electrical contact terminals are spaced apart on the applicator by a distance corresponding to a rest spacing between blades of a given bipolar forceps.

3. A surgical bone wax applicator according to claim 2, wherein the heating wire has a substantially non-inductive load impedance so that the heating wire is energizable by a given bipolar generator.

4. A surgical bone wax applicator according to claim 1, wherein the absorbent material comprises cotton.

5. A surgical bone wax applicator according to claim 1, including a radiopaque marker disposed on the absorbent material.

6. A set of surgical bone wax applicators comprising a plurality of the bone wax applicators according to claim 1, wherein each of the applicators of the set has a different associated identifier to distinguish the applicator from remaining applicators of the set.

7. A system for applying bone wax on bone tissue to effect hemostasis, comprising:
   a surgical bone wax applicator having one or more layers of an absorbent material, a mass of bone wax adhered on the absorbent material, and an electrical heating element disposed within the absorbent material;
   the heating element comprises an electrically resistive heating wire or conductor that extends within the absorbent material in the vicinity of the mass of bone wax, and the heating wire has an associated pair of electrical contact terminals that are exposed on the applicator for connecting the heating wire to an outside voltage source;
   the heating wire is constructed and arranged to heat and soften the mass of bone wax when the electrical contact terminals of the heating wire are connected to the outside voltage source and a determined current flows through the heating wire;
   a bipolar generator constructed and arranged to supply a certain output voltage;
   bipolar forceps having a pair of opposed electrical contact blades for applying the output voltage from the bipolar generator;
   a cable arranged for connecting the output voltage from the bipolar generator to the contact blades of the bipolar forceps; and
   the electrical contact terminals of the heating wire are disposed on the applicator for contacting the electrical contact blades of the bipolar forceps so that the output voltage from the bipolar generator is applied to the heating wire and said determined current flows through the heating wire when the bipolar generator is activated.

8. A system according to claim 7, wherein the heating wire of the bone wax applicator has a substantially non-inductive load impedance.

9. A system according to claim 7, wherein the heating wire of the bone wax applicator comprises an electrically resistive conductor.

10. A surgical bone wax applicator according to claim 1, wherein the absorbent material is in the form of an elongate strip, and the mass of bone wax is disposed at or near each end of the strip.

11. A surgical bone wax applicator according to claim 1, wherein the absorbent material is in the form of an elongate strip, and two or more masses of bone wax are disposed at or near each end of the strip.

12. A system according to claim 7, wherein the absorbent material of the bone wax applicator is in the form of an elongate strip, and the mass of bone wax is disposed at or near each end of the strip.

13. A system according to claim 7, wherein the absorbent material of the bone wax applicator is in the form of an elongate strip, and two or more masses of bone wax are disposed at or near each end of the strip.

14. A system for applying bone wax on bone tissue to effect hemostasis, comprising:
a surgical bone wax applicator having one or more layers of an absorbent material, a mass of bone wax adhered on the absorbent material, and an electrical heating element disposed within the absorbent material;
the heating element comprises an electrically resistive heating wire or conductor that extends within the absorbent material in the vicinity of the mass of bone wax, and the heating wire has an associated pair of electrical contact terminals that are exposed on the applicator for connecting the heating wire to an outside voltage source;
the heating wire is constructed and arranged to heat and soften the mass of bone wax when the electrical contact terminals of the heating wire are connected to the outside voltage source and a determined current flows through the heating wire;
a voltage source constructed and arranged to supply a certain output voltage;
forceps arranged for electrical connection to the voltage source and having a pair of electrical contact blades for applying the output voltage from the voltage source; and
the electrical contact terminals of the heating wire are disposed on the applicator for contacting the electrical contact blades of the forceps, so that the output voltage of the voltage source is applied to the heating wire and said determined current flows through the heating wire when the voltage source is activated.

15. A system according to claim 14, wherein the voltage source has an associated switch arranged for activating the voltage source.

16. A system according to claim 14, including a radiopaque marker disposed on the absorbent material of the bone wax applicator.

17. A system according to claim 14, including a package of a number of the bone wax applicators, wherein each applicator in the package has a different identifier to distinguish the applicator from other applicators in the package.

18. A surgical bone wax applicator according to claim 1, wherein the heating element comprises a strip of electrically insulated heat resistant material, and the heating wire and the associated contact terminals are formed on the strip.

19. A system according to claim 7, wherein the heating element comprises a strip of electrically insulated heat resistant material, and the heating wire and the associated contact terminals are formed on the strip.

20. A system according to claim 14, wherein the heating element comprises a strip of electrically insulated heat resistant material, and the heating wire and the associated contact terminals are formed on the strip.

* * * * *